United States Patent
Aoki

(10) Patent No.: US 8,736,284 B2
(45) Date of Patent: May 27, 2014

(54) PARTICULATE MATTER DETECTION DEVICE

(75) Inventor: Keiichiro Aoki, Sunto-gun (JP)

(73) Assignee: Toyota Jidosha Kabushiki Kaisha, Toyota-shi (JP)

(*) Notice: Subject to any disclaimer, the term of this patent is extended or adjusted under 35 U.S.C. 154(b) by 365 days.

(21) Appl. No.: 13/057,174

(22) PCT Filed: Jan. 8, 2010

(86) PCT No.: PCT/JP2010/050158
§ 371 (c)(1),
(2), (4) Date: Aug. 10, 2011

(87) PCT Pub. No.: WO2011/083581
PCT Pub. Date: Jul. 14, 2011

(65) Prior Publication Data
US 2011/0285410 A1   Nov. 24, 2011

(51) Int. Cl.
*G01R 27/26* (2006.01)
(52) U.S. Cl.
USPC ............... 324/686; 324/464; 324/71.1
(58) Field of Classification Search
USPC ........... 324/464, 71.1, 686, 691; 205/785.5, 205/786; 73/865.5
See application file for complete search history.

(56) References Cited

U.S. PATENT DOCUMENTS

| 3,710,615 A | * | 1/1973 | Johnson et al. ............... 73/61.75 |
| 4,505,783 A | * | 3/1985 | Mase et al. .................. 205/785 |
| 2003/0102854 A1 | | 6/2003 | Gascoyne et al. |

FOREIGN PATENT DOCUMENTS

| JP | 8 128979 | 5/1996 |
| JP | 2005 512042 | 4/2005 |
| JP | 2006 515066 | 5/2006 |
| JP | 2007 078520 | 3/2007 |
| JP | 2008 64621 | 3/2008 |
| JP | 2009 23883 | 2/2009 |
| JP | 2009 31213 | 2/2009 |
| WO | 2008 096853 | 8/2008 |

OTHER PUBLICATIONS

International Search Report issued Mar. 9, 2010 in PCT/JP10/050158 filed Jan. 8, 2010.

* cited by examiner

*Primary Examiner* — Vincent Q Nguyen
(74) *Attorney, Agent, or Firm* — Oblon, Spivak, McClelland, Maier & Neustadt, L.L.P.

(57) ABSTRACT

A particulate matter detection device that detects the diameter and the amount of particulates in exhaust gas while reducing detection error caused by deterioration such as the deterioration of electrodes is provided. In the particulate matter detection device, which measures particulates in a gaseous body, AC voltages having different frequencies are applied to a pair of electrodes disposed apart from each other. The resulting impedances to the different frequencies are detected. A resistance component and/or a capacitance component of the impedances to the different frequencies are calculated. The average diameter and/or the number of particulates in the gaseous body are estimated in accordance with changes in the resistance component and/or the capacitance component.

9 Claims, 5 Drawing Sheets

R1: PM internal resistance component
C1: PM internal capacitance component
R2: PM particle boundary resistance component
C2: PM particle boundary capacitance component
Re: electrode resistance component

PARTICULATE MATTER DETECTION DEVICE

TECHNICAL FIELD

The present invention relates to a particulate matter detection device, and more particularly, to a particulate matter detection device that is installed in an exhaust path of an internal combustion engine and suitable for detecting particulate matter in exhaust gas.

BACKGROUND ART

A conventional particulate sensor for detecting the amount of particulate matter in exhaust gas of an internal combustion engine is disclosed, for instance, in Patent Document 1. This sensor includes electrodes that are disposed parallel to each other with a space in between. The sensor is installed in an exhaust path in such a manner that at least some portions of the electrodes are exposed to the exhaust gas. When the exhaust gas is discharged through the exhaust path, particulate matter in the exhaust gas deposits on the electrodes. This causes the impedance between the electrodes to change. The sensor disclosed in Patent Document 1 detects changes in the impedance to determine the amount of particulate matter deposited between the electrodes.

PRIOR ART LITERATURE

Patent Document

Patent Document 1: JP-A-2006-515066

SUMMARY OF THE INVENTION

Problem to be Solved by the Invention

By the conventional sensor disclosed in Patent Document 1, the amount of particulate matter in a gaseous body can be detected in accordance with changes in the impedance, but the diameter or the number of particulates in the gaseous body cannot be estimated. Meanwhile, a particulate meter based, for instance, on laser light is known as a device for measuring the number of particulates in a gaseous body. However, it is difficult to use this device as a vehicle-mounted device or other on-board device because it is large-sized and expensive. Under these circumstances, an easy-to-use device capable of determining not only the amount of particulate matter contained in a gaseous body but also the number and the diameter of particulates is demanded.

Further, by the conventional sensor disclosed in Patent Document, the amount of particulate matter are measured in accordance with the impedance of the entire circuit including sensor electrodes and lead wires (hereinafter referred to as the electrodes and the like). Therefore, the amount of change in the impedance (the difference from an initial value) includes not only the amount of change caused by particulate matter deposition but also the amount of change caused, for instance, by the deterioration of the electrodes and the like. Moreover, if the electrodes and the like significantly deteriorate, the amount of impedance change caused by the deterioration of the electrodes and the like accounts for a relatively large portion of the detected amount of impedance change. In such an instance, it is conceivable that the amount of particulate matter calculated from the amount of impedance change may significantly differ from the actual amount of particulate matter.

The present invention has been made to address the above problem. An object of the present invention is to provide an improved particulate matter detection device that is capable of detecting the diameter and the amount of particulates in the exhaust gas while reducing detection error caused by deterioration such as the deterioration of the electrodes.

Means for Solving the Problem

In accomplishing the above object, according to a first aspect of the present invention, there is provided a particulate matter detection device for measuring particulates in a gaseous body, the particulate matter detection device including: frequency control means for controlling the frequency of an AC voltage applied to a pair of electrodes disposed apart from each other; AC impedance detection means for detecting impedances to different frequencies when AC voltages having the different frequencies are applied; component calculation means for calculating a resistance component and/or a capacitance component of the impedances to the different frequencies; and particulate diameter estimation means for estimating the average diameter and/or the number of particulates in the gaseous body in accordance with changes in the resistance component and/or changes in the capacitance component.

According to a second aspect of the present invention, there is provided the particulate matter detection device as described in the first aspect, when calculating the resistance component and/or the capacitance component, which each include an intraparticle component and a particle boundary component, the component calculation means calculates the intraparticle component, which is attributable to the internal characteristics of particulates, and the particle boundary component, which is attributable to the interfacial characteristics between particulates. And, the particulate diameter estimation means estimates the average diameter and/or the number of particulates in accordance with the result of comparison between the intraparticle component and the particle boundary component.

According to a third aspect of the present invention, there is provided the particulate matter detection device as described in the first or the second aspect, the particulate matter detection device further including: particulate matter amount estimation means for estimating the amount of particulate matter in the gaseous body in accordance with the intraparticle component and the particle boundary component, which are included in the resistance component.

According to a fourth aspect of the present invention, there is provided the particulate matter detection device as described in the first aspect, the particulate matter detection device further including: inter-electrode resistance detection means for detecting the resistance between the electrodes; and particulate matter amount estimation means for estimating the amount of particulate matter in the gaseous body in accordance with the detected inter-electrode resistance.

According to a fifth aspect of the present invention, there is provided the particulate matter detection device as described in the fourth aspect, the particulate matter detection device further including: saturation judgment means for judging whether the estimated particulate matter amount has reached a reference amount indicative of saturation, wherein, when it is concluded that the particulate matter amount has reached the reference amount, the AC impedance detection means performs an impedance detection process.

According to a sixth aspect of the present invention, there is provided a particulate matter detection device for measuring particulates in a gaseous body, the particulate matter detection device including: frequency control means for controlling the frequency of an AC voltage applied to a pair of electrodes disposed apart from each other; AC impedance detection means for detecting impedances to different frequencies when AC voltages having the different frequencies are applied; particle resistance component calculation means for calculating a resistance component of the impedances to the different frequencies while a particle resistance component attributable to the internal characteristics and interfacial characteristics of particulates is distinguished from components attributable to the others; and particulate matter amount estimation means for estimating the amount of particulate matter in accordance with the particle resistance component included in the resistance component.

Advantageous Effects of Invention

According to the first aspect of the present invention, the average diameter or the number of particulates can be estimated by detecting changes in the resistance component and/or capacitance component of the impedance detected when AC voltages having different frequencies are applied to a pair of electrodes. Therefore, when the small-size device having the pair of electrodes is used, the diameter or the number of particulates can be detected with ease.

According to the second aspect of the present invention, the intraparticle component, which is attributable to the internal characteristics of particulates, and the particle boundary component, which is attributable to the interfacial characteristics between particulates, are separately calculated when the resistance component and/or the capacitance component, which each include the intraparticle component and the particle boundary component, are calculated. Here, the portion of the intraparticle component increases with an increase in the particulate diameter, and the portion of the particle boundary component increases with a decrease in the particulate diameter, which increases the contact interface between particulates. Therefore, the average diameter or the number of particulates can be estimated with increased certainty when the second aspect of the present invention compares the intraparticle component with the particle boundary component.

The intraparticle component and particle boundary component included in the resistance component are derived from the particulates between the electrodes and do not include changes in the resistance of the electrodes and the like of the device. Consequently, according to the third aspect of the present invention, the amount of particulate matter can be estimated with increased accuracy without being significantly affected by resistance changes caused by deterioration of the electrodes and the like as far as the amount of particulate matter is estimated in accordance with the intraparticle component and particle boundary component.

According to the fourth aspect of the present invention, the amount, the average diameter, and the number of particulates can be detected with one detection device.

According to the fifth aspect of the present invention, the AC impedance detection process is performed when it is recognized that the particulates are deposited to saturation. This makes it possible to reduce the influence of impedance changes during a particulate deposition process and accurately estimate the average diameter and the number of particulates with increased stability.

According to the sixth aspect of the present invention, the resistance component of the impedance to a changing frequency is calculated while the particle resistance component attributable to the internal characteristics and interfacial characteristics of particulates is distinguished from components attributable to the others. The amount of particulate matter is then estimated in accordance with the particle resistance component included in the resistance component. This makes it possible to eliminate the influence of resistance changes caused, for instance, by the deterioration of the electrodes and detect the amount of particulate matter with increased accuracy.

MODE FOR CARRYING OUT THE INVENTION

Figure 1:
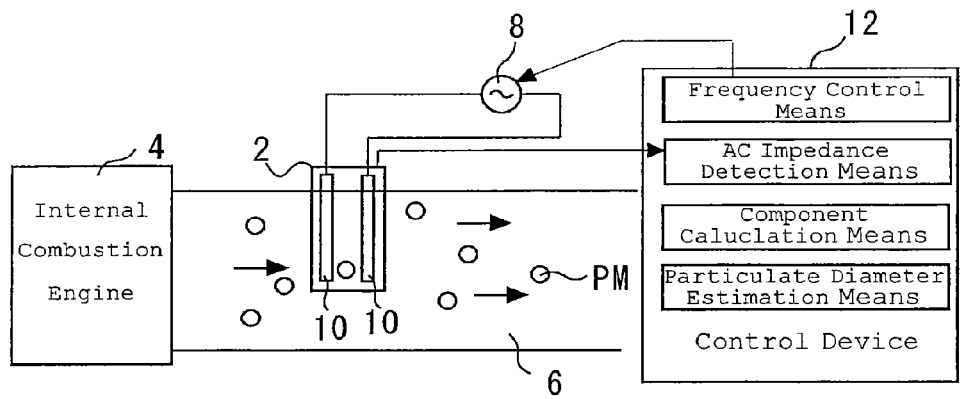
FIG. 1 is a schematic diagram illustrating total construction of a system of a first embodiment of the present invention.

Embodiments of the present invention will now be described with reference to the accompanying drawings. Like elements or corresponding elements in the drawings are designated by the same reference numerals and will be described in an abbreviated manner or will not be redundantly described.

First Embodiment

FIG. 1 is a schematic diagram illustrating how a PM sensor according to a first embodiment of the present invention is installed. As shown in FIG. 1, the PM sensor 2 is installed in an exhaust path 6 of an internal combustion engine 4 mounted, for instance, on a vehicle. The PM sensor 2 (particulate matter detection device) is connected to an AC power supply 8 that applies an AC voltage and a DC voltage. The PM sensor 2 includes a pair of electrodes 10 that are disposed apart from each other. The PM sensor 2 is installed in the exhaust path 6 in such a manner that at least some portions of the electrodes 10 are exposed to exhaust gas. The PM sensor 2 is also connected, for instance, to an impedance detector (not shown), which detects the impedance between the electrodes 10, and to a frequency detector (not shown), which detects an AC frequency.

The system shown in FIG. 1 includes a control device 12. The control device 12 is connected, for instance, to various detectors for the PM sensor 2 and to the AC power supply 8. The control device 12 not only receives output signals from these detectors to detect, for instance, the AC impedance of the PM sensor 2, but also performs various computations as needed and issues a control signal to the AC power supply 8 to control, for instance, the frequency of the voltage to be applied to the PM sensor 2.

Figure 2A:
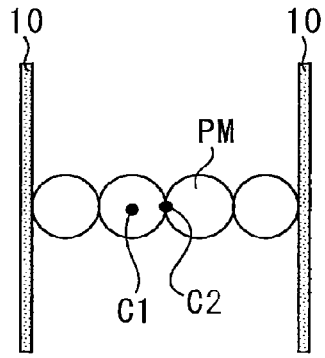
FIG. 2 is a schematic diagram illustrating the PM sensor according to the first embodiment of the present invention.
Figure 2B:
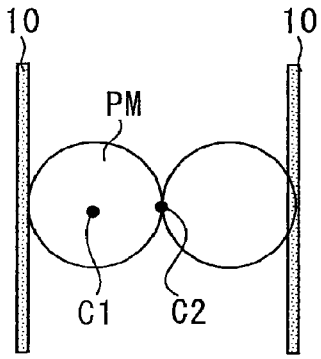

FIGS. 2(a) and 2(b) are schematic diagrams illustrating the PM sensor 2 according to the first embodiment of the present invention. As shown in FIGS. 2(a) and 2(b), the pair of electrodes 10 included in the PM sensor 2 are disposed parallel to each other with a predetermined space in between. The PM sensor 2 is installed so that at least some portions of the electrodes 10 are exposed to the exhaust gas.

PM (particulate matter) exists in the exhaust gas of the internal combustion engine 4. The PM deposits on the electrodes 10 included in the PM sensor 2. FIG. 2(a) shows a situation where the PM deposited between the electrodes 10 for the PM sensor 2 is relatively small, whereas FIG. 2(b) shows a situation where the deposited PM is relatively large. FIGS. 2(a) and 2(b) indicate that PM particles deposited between the electrodes 10 have substantially the same particle diameter. In reality, however, the deposited PM particles vary in particle diameter. For the sake of simplicity, FIG. 2(a) schematically shows a situation where the average PM diameter is relatively small, whereas FIG. 2(b) schematically shows a situation where the average PM diameter is relatively large. The amount and the average diameter or the number of PM particles deposited between the electrodes 10 as shown in FIGS. 2(a) and 2(b) are detected by the PM sensor 2 in a manner described below.

The resistance component and capacitance component generated when an AC voltage is applied to the PM sensor 2 can be classified into the following three components in the PM sensor 2.

(1) Component attributable to the characteristics within a PM particle (intraparticle component)
(2) Component attributable to the characteristics of contact interface (particle boundary) between PM particles (particle boundary component)
(3) Non-PM components such as the components of the electrodes 10 and lead wires for the PM sensor 2

Figure 3:
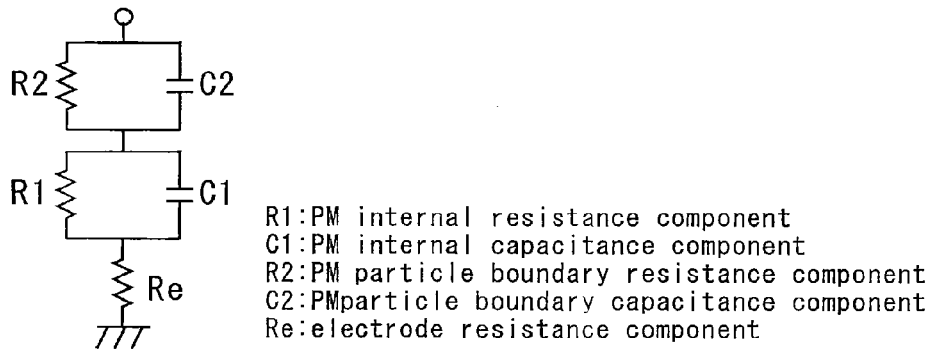
FIG. 3 is a schematic diagram illustrating the equivalent circuit diagram of the PM sensor 2 in PM deposited state, according to the first embodiment of the present invention.

Here, the capacitance component of the electrodes and the like (3) can be ignored. Therefore, the PM sensor 2 can be indicated by an equivalent circuit diagram shown in FIG. 3. In the equivalent circuit diagram shown in FIG. 3, a PM internal resistance component R1 and a PM internal capacitance component C1 are components attributable to the characteristics within a PM particle (1); a PM particle boundary resistance component R2 and a PM particle boundary capacitance component C2 are components attributable to the PM particle boundary characteristics (2); and an electrode resistance component Re is a resistance component derived from the non-PM components such as the components of the electrodes and the like (3).

The PM internal resistance component R1, the PM particle boundary resistance component R2, the PM internal capacitance component C1, and the PM particle boundary capacitance component C2 vary not only with the amount of deposited PM but also with the diameter (size) of the PM. When, for instance, the particle diameter of the PM decreases (as indicated in FIG. 2(a)), the area of the PM particle boundary increases. The characteristics of the PM particle boundary then exercise greater influence upon the entire circuit. Therefore, when PM particle boundary components are compared with PM internal components, the portions of the PM particle boundary resistance component R2 and PM particle boundary capacitance component C2 are relatively large, whereas the portions of the PM internal resistance component R1 and PM internal capacitance component C1 are relatively small.

When, in contrast, the particle diameter of the PM increases (as indicated in FIG. 2(b)), the influence of electron conductivity within the PM becomes greater. Therefore, when the PM particle boundary components are compared with the PM internal components, the portions of the PM internal resistance component R1 and PM internal capacitance component C1 are relatively large, whereas the portions of the PM particle boundary resistance component R2 and PM particle boundary capacitance component C2 are relatively small.

When the above analysis is used to detect and compare the magnitudes of resistances (or capacitances) of the PM particle boundary components and PM internal components, it is possible to estimate not only the amount of deposited PM but also the average particle diameter of the PM. Under the above circumstances, the first embodiment detects, for instance, the resistance of the aforementioned components (1) to (3) as described below.

Figure 4:
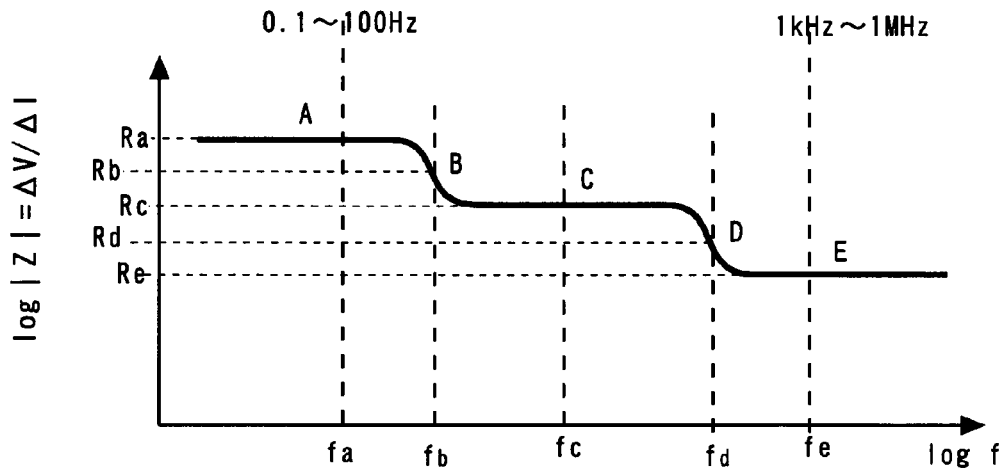
FIG. 4 is a diagram illustrating impedance changes of the PM sensor in response to the change of AC frequency, according to the first embodiment of the present invention.

FIG. 4 shows how impedance changes when an AC voltage is applied to the PM sensor 2 according to the first embodiment of the present invention while its frequency is varied (swept) from low to high at fixed intervals. In FIG. 4, the horizontal axis represents the logarithm of the frequency (log f) and the vertical axis represents the logarithm of the impedance ($\log|z| = \Delta V / \Delta I$). When the frequency of an AC voltage applied to the PM sensor 2 increases, the impedance ideally changes in a stepwise fashion as shown in FIG. 4.

Figure 5:
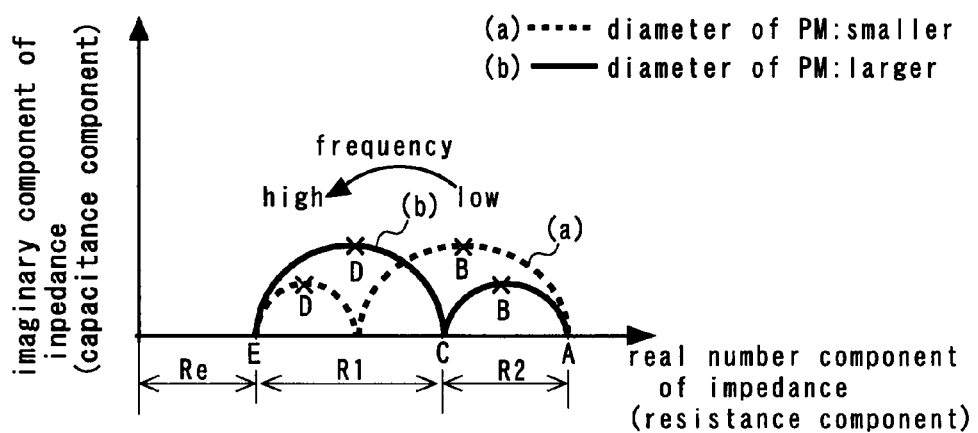
FIG. 5 is a diagram illustrating the impedance changes of the PM sensor in response to the changes of frequency, according to the first embodiment of the present invention.

FIG. 5 shows a complex impedance plot that shows how impedance changes when an AC voltage is applied to the PM sensor 2 with its frequency continuously varied (swept) as shown in FIG. 4. In FIG. 5, the horizontal axis represents a real number component (resistance component) of the impedance and the vertical axis represents an imaginary component (capacitance component).

Resistances Ra, Rc, and Rd are calculated from the intersection between the x-axis and a curve indicative of complex impedance. Resistance Ra (resistance value of area A in FIG. 4), which is detected upon the application of low-frequency AC voltage, is the resistance obtained by adding all resistance components. It means that Ra=Re+R1+R2. Resistance Rc is equal to Re+R1. Resistance Re is an electrode resistance component Re. Thus, the values R1, R2, and Re are calculated from the values Ra, Rc, and Rd.

Further, the frequency fb prevailing when an average resistance value Rb=Re+R1+R2/2 is calculated, for instance, by linear approximation or interpolation. From the thus calculated value, the PM particle boundary capacitance component C2 is calculated in accordance with the equation R2C2=1/($2\pi$fb). Furthermore, the frequency fd prevailing when an average resistance value Rd=Re+2/R1 is calculated, for instance, by linear approximation or interpolation. From the thus calculated value, the PM particle boundary capacitance component C2 is calculated in accordance with the equation R2C2=1/($2\pi$fd).

When the particle diameter is small as indicated by the broken line (a) in FIG. 5, the influence of the PM particle boundary becomes greater to decrease the PM internal resistance component R1 and PM internal capacitance component C1, thereby increasing the PM particle boundary resistance component R2 and PM particle boundary capacitance component C2. When, in contrast, the particle diameter is increased as indicated by the solid line (b) in FIG. 5, the influence of PM internal characteristics becomes greater to increase the PM internal resistance component R1 and PM internal capacitance component C1, thereby decreasing the PM particle boundary resistance component R2 and PM particle boundary capacitance component C2.

Figure 6:
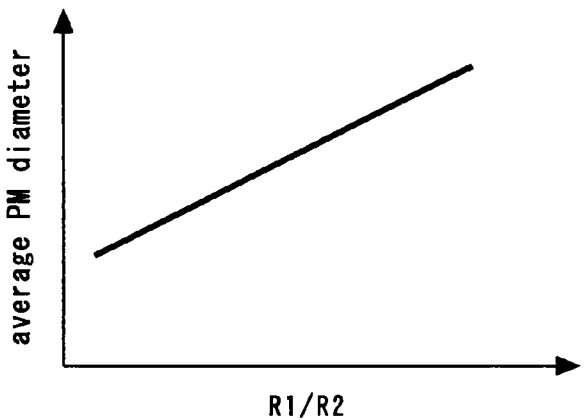
FIG. 6 is a diagram illustrating the relationship between the ratio of the resistance and the average diameter of the PM, according to the first embodiment of the present invention.

FIG. 6 shows the relationship between the ratio of the PM internal resistance component R1 to the PM particle boundary resistance component R2 and the average diameter of the PM. In FIG. 6, the horizontal axis represents the resistance ratio R1/R2 and the vertical axis represents the average PM diameter. As shown in FIG. 6, the average PM diameter correlates with the resistance ratio R1/R2. When the resistance ratio R1/R2 increases, that is, the portion of the PM internal resistance component R1 increases, the average PM diameter increases.

In the first embodiment, the relationship between the resistance ratio R1/R2 and the average PM diameter is predetermined, for instance, by experiment and stored in the control device 12 as a map. While the internal combustion engine 4 is operating, an AC voltage is applied with the frequency continuously varied from low to high to measure the resulting impedance values. The impedance characteristics shown, for instance, in FIG. 5 are then predicted to calculate the resistance components R1, R2. Subsequently, the resistance ratio R1/R2 is calculated to calculate the PM particle diameter.

The resistance of the PM sensor 2 varies with the amount of PM deposited between the electrodes 10. It should be noted, however, that the changes in the resistance of the PM sensor 2 include changes in the electrode resistance component Re, which is a non-PM component. In the first embodiment, therefore, a PM combustion process is performed when the PM deposited on the electrodes 10 becomes saturated, and initial resistance Ri prevailing immediately after the combustion process is detected at the end of each combustion process. As no PM is deposited on the electrodes 10 at the end of the PM combustion process, the above-mentioned initial resistance is equivalent to the electrode resistance component Re.

When the amount of particulates is to be detected, a DC voltage is applied to the PM sensor 2 to detect actual resistance Rm. The amount of particulates is then detected in accordance with resistance Rm−Ri, which is determined by subtracting the initial resistance Ri from the actual resistance Rm. As this excludes resistance equivalent to the electrode resistance component Re, the amount of deposited PM can be properly estimated while the influence of the deterioration of the electrodes and the like is reduced. The relationship between the resistance Rm−Ri and the amount of deposited PM should be predetermined, for instance, by experiment and stored in the control device 12 as a map. When the actual amount of deposited PM is to be detected, the amount of PM is calculated from the map in accordance with the detected resistance Rm−Ri. Further, in the first embodiment, the number of PM particles can also be calculated because the average diameter and the amount of PM are simultaneously determined.

Figure 7:
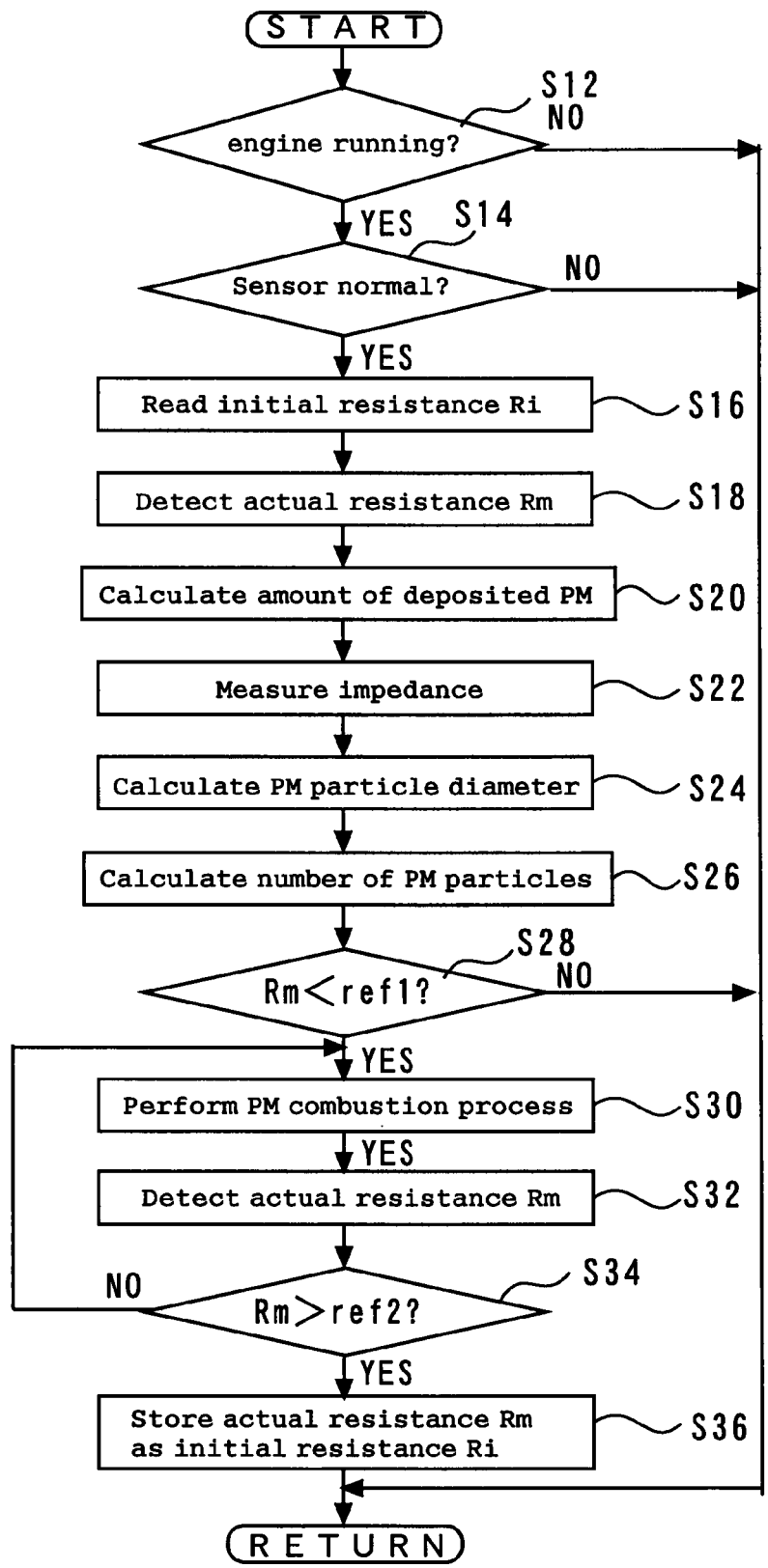
FIG. 7 is a flow diagram illustrating a control routine that is executed by the system in accordance with the first embodiment of the present invention.

FIG. 7 shows a control routine that the control device executes in accordance with the first embodiment of the present invention. The routine shown in FIG. 7 is repeatedly executed at fixed intervals while the internal combustion engine 4 operates. First of all, the routine shown in FIG. 7 performs step S12 to detect whether the internal combustion engine 4 is running. If the internal combustion engine 4 is stopped, the routine terminates because the PM need not be detected.

If, in contrast, the internal combustion engine 4 is found to be running, the routine proceeds to step S14 and judges whether the PM sensor 2 is normal. If, for instance, the PM sensor 2 is still not warmed up to its activation temperature, it is concluded that the PM sensor 2 is not normal. If the PM sensor 2 is not found to be normal, the routine terminates.

If, in contrast, the PM sensor 2 is found to be normal in step S14, the routine reads the initial resistance Ri. The initial resistance Ri is factory adjusted to resistance that prevails when a DC voltage is applied to the PM sensor 2. When the routine is executed subsequently, the initial resistance Ri is detected and updated during a later-described process.

Next, the routine performs step S18 to detect the actual resistance Rm that prevails when a DC voltage is applied between the electrodes 10. The routine then proceeds to step S20 and calculates the amount of deposited PM. The amount of deposited PM is calculated in accordance with the resistance Rm−Ri, which is obtained by subtracting the initial resistance Ri from the actual resistance Rm. The initial resistance Ri is an impedance that is detected while no PM is deposited on the electrodes 10. Therefore, when the amount of deposited PM is determined in accordance with the resistance Rm−Ri, the amount of PM is accurately calculated. More specifically, the control device 12 calculates the amount of deposited PM from the resistance Rm−Ri in accordance with the stored map indicating the correlation between resistance and the amount of PM.

Next, the routine proceeds to step S22 and measures the impedance. In this step, the impedance is detected by applying an AC voltage while its frequency is continuously varied. When this step is completed, the resistance components R1, R2 are detected.

Next, the routine proceeds to step S24 and computes the average diameter of PM. The average PM diameter is calculated from the map stored in the control device 12 in accordance with the ratio between the resistance components R1, R2. Next, the routine performs step S26 to calculate the number of PM particles. The number of PM particles is determined by dividing the amount of deposited PM by a cubic volume determined from the average PM diameter.

Next, the routine proceeds to step S28 and judges whether the deposited PM is saturated. More specifically, the routine judges whether the actual resistance Rm determined in step S18 is smaller than a first reference resistance ref1. The first reference resistance ref1 is stored in the control device 12 and set to a value close to the maximum resistance prevailing when the amount of PM deposited in the PM sensor 2 is saturated. If the actual resistance Rm is not smaller than the first reference resistance ref1 in step S28, the routine terminates its process.

If, in contrast, the actual resistance Rm is smaller than the first reference resistance ref1 in step S28, the routine proceeds to step S30 and performs a PM combustion process for the PM deposited on the electrodes. The routine then proceeds to step S32 and detects the actual resistance Rm.

Next, the routine performs step S34 to judge whether the detected actual resistance Rm is greater than a second reference resistance ref2. The second reference resistance ref2 is stored in the control device 12 and set to a value close to the minimum resistance that the PM sensor 2 indicates when no PM is deposited in the PM sensor 2.

If the actual resistance Rm is not greater than the second reference resistance ref2 in step S34, the routine concludes that the PM combustion process may not sufficiently be performed, returns to step S30, and performs the PM combustion process for a predetermined period of time. The routine then performs step S32 to detect the actual resistance Rm, and performs step S34 to judge whether the detected actual resistance Rm is greater than the second reference resistance ref2. The steps for performing the PM combustion process (S30), detecting the actual resistance Rm (S32), and judging whether the PM is burned (S34) are repeatedly performed until the actual resistance Rm is greater than the second reference resistance ref2.

If, in contrast, the actual resistance Rm is greater than the second reference resistance ref2 in step S34, the routine concludes that the PM combustion process is completed, and performs step S36 to store the current actual resistance Rm as the initial resistance Ri. Upon completion of step S36, the routine terminates its process.

As described above, the first embodiment makes it possible to continuously vary the frequency and detect the resulting impedance changes for the purpose of separately detecting the resistance attributable to the inside of the PM and the resistance attributable to the particle boundary of the PM. Therefore, the first embodiment can detect not only the amount of deposited PM but also the average diameter of the PM and the number of PM particles.

Further, the first embodiment can apply an AC voltage while continuously varying its frequency, measure the impedance, and separately detect the resistance attributable to the electrodes 10 and the like and the resistance attributable to the PM (the inside and the particle boundary of the PM). Therefore, the resistance component derived from the electrodes 10 and the like can be removed from the detected resistance and capacitance. This makes it possible to eliminate the influence of error in the PM sensor 2, which may be caused, for instance, by the deterioration of the electrodes, and estimate the average PM diameter and the number of PM particles with increased accuracy.

However, the present invention is not limited to a sensor that eliminates the influence of the deterioration of the electrodes 10 and the like, but is also applicable to a sensor that estimates the average PM diameter and the number of PM particles without considering the deterioration of the electrodes 10 and the like.

The first embodiment subtracts the initial resistance Ri, which is stored as the impedance prevailing immediately after PM combustion, from the actual resistance Rm, which is a measured impedance, and calculates the amount of deposited PM in accordance with the resistance Rm−Ri. This makes it possible to eliminate the influence of error in the PM sensor 2, which may be caused by the deterioration of the electrodes and the like, and accurately estimate the amount of deposited PM.

In the first embodiment, it is assumed that the amount of deposited PM is determined by detecting the resistance (actual resistance Rm and initial resistance Ri) prevailing upon DC voltage application in addition to impedance measurement for average PM diameter calculation. However, an alternative, for example, is to detect a resistance component from an impedance encountered when an AC voltage having a predetermined frequency is applied, and detect the amount of deposited PM in accordance with the detected resistance component.

Further, the amount of deposited PM can also be estimated in accordance with the PM internal resistance component R1 and PM particle boundary resistance component R2 (particle resistance component), which are determined during impedance measurement for average PM diameter calculation. As the amount of PM can be calculated in this manner with the electrode resistance component Re excluded, the amount of deposited PM can be estimated by eliminating the influence of the deterioration of the electrodes and the like.

The present invention can also be applied to a sensor that detects only the amount of deposited PM and does not estimate the average PM diameter and the number of PM particles. Even when the present invention is applied to a sensor that detects only the amount of deposited PM, the influence, for instance, of the deterioration of the electrodes 10 and the like can be reduced to accurately detect the amount of deposited PM by using the resistance obtained by subtracting the initial resistance Ri from the actual resistance Rm or by using only the resistance components R1, R2 derived from the PM particles.

It should be noted, however, that the present invention is not limited to a sensor that eliminates the influence of the deterioration of the electrodes 10 and the like. The present invention can also be applied to a sensor that, for example, estimates the amount of deposited PM without considering the deterioration of the electrodes 10 and the like.

In the first embodiment, it is also assumed that the average PM diameter is estimated in accordance with the ratio between the PM internal resistance component R1 and PM particle boundary resistance component R2. However, as shown in FIG. 5, the PM internal capacitance component C1 increases when the PM is large, and the PM particle boundary capacitance component C2 increases when the PM is small. Therefore, the average PM diameter can also be calculated by comparing the capacitance components C1, C2. It should be noted that the capacitance components C1, C2 can be calculated by calculating the resistances Rb, Rd and the prevailing frequencies fb, fd.

Furthermore, the first embodiment detects an impedance value prevailing when an AC voltage is applied while its frequency is continuously varied from low to high, roughly predicts the impedance characteristics, and separately detects the resistance components R1, R2 and the capacitance components C1, C2. However, the present invention is not limited to the use of such a scheme. An alternative, for example, is to predefine a plurality of frequencies for estimating the resistance components R1, R2, Re and the capacitance components C1, C2, and apply only AC voltages having the predefined frequencies. The predefined frequencies may be, for example, two or three different frequencies. More specifically, for instance, the range of frequencies fa, fc, fe corresponding to the resistance values Ra, Rc, Re in FIG. 4 can be predicted to a certain extent. Therefore, when frequencies within the predictable range are predetermined and AC voltages having the predetermined frequencies are applied, it is possible to estimate, for example, the resistance components R1, R2, Re.

The "inter-electrode resistance detection means" according to the present invention is implemented when the process in step S18 is performed. The "particulate matter amount estimation means" is implemented when the process in step S20 is performed. The "AC impedance detection means" is implemented when the process in step S22 is performed. The "particulate matter diameter estimation means" is implemented when step S24 or S26 is performed.

Second Embodiment

Figure 8:
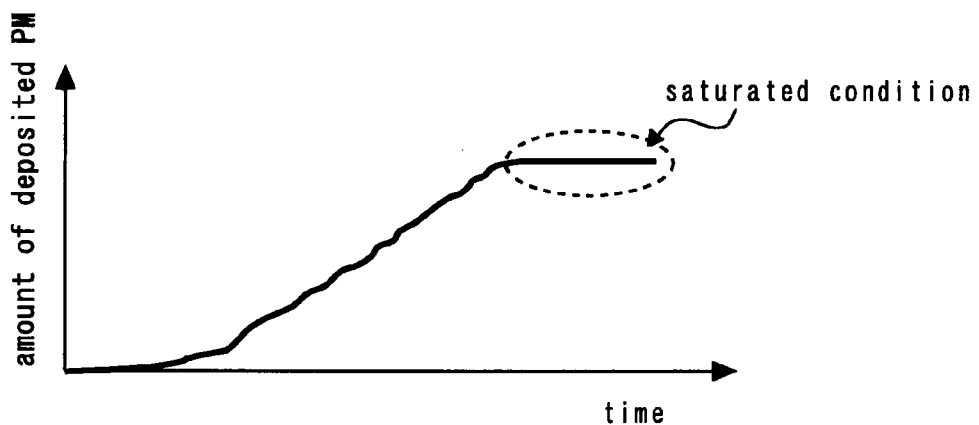
FIG. 8 is a diagram illustrating the amount of PM deposited and elapsed time according to the second embodiment of the present invention.

A second embodiment of the present invention will now be described. The system according to the second embodiment is the same as the system according to the first embodiment except that the timing for calculating the number of PM particles is specified. FIG. 8 shows how the amount of PM deposited in the PM sensor 2 changes with time. In FIG. 8, the horizontal axis represents time and the vertical axis represents the amount of deposited PM.

As shown in FIG. 8, the amount of PM deposited in the PM sensor 2 increases with time. However, when it is saturated, it does not increase any more and remains constant. The resistance of the PM sensor 2 varies in accordance with the amount of deposited PM. Therefore, when the amount of deposited PM becomes saturated and remains constant, the resistance of the PM sensor 2 does not vary and remains constant.

In the second embodiment, when the actual resistance Rm of the PM sensor 2 is saturated, an AC voltage is applied to the PM sensor 2 with its frequency continuously varied to measure the impedance. This ensures that impedance measurements can be made in a stable manner. Consequently, the average PM diameter and the number of PM particles can be estimated with increased accuracy.

Figure 9:
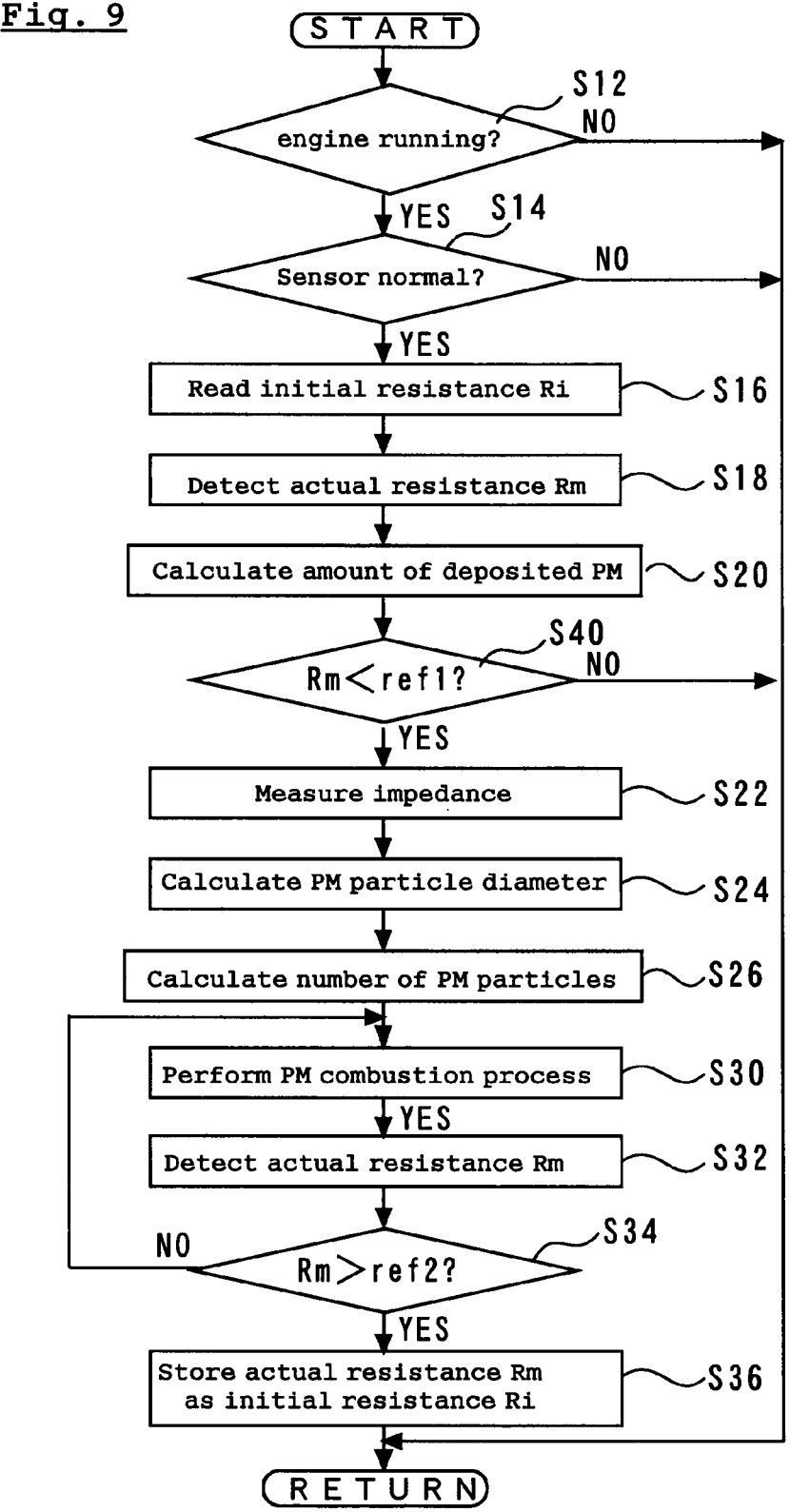
FIG. 9 is a flow diagram illustrating a control routine that is executed by the system according to the second embodiment of the present invention.

FIG. 9 shows a control routine that is executed by the system according to the second embodiment of the present invention. The routine shown in FIG. 9 is the same as the routine shown in FIG. 7 except that the process in step S28 is performed immediately after step S20.

More specifically, after step S20 is completed to calculate the amount of deposited PM in the same manner as in the first embodiment, step S40 is performed to judge whether the current amount of deposited PM is saturated, that is, whether the actual resistance Rm minus the initial resistance Ri is smaller than the first reference resistance ref1. If the resistance Ra minus the initial resistance Ri is not smaller than the first reference resistance ref1, the routine concludes that the amount of deposited PM is still not saturated, and terminates the current process without making impedance measurements and the like.

If, in contrast, the actual resistance Rm minus the initial resistance Ri is smaller than the first reference resistance ref1, the routine performs step S22 to make impedance measurements and then performs steps S24 and S26 to calculate the average PM diameter and the number of PM particles, as is the case with the first embodiment. Subsequently, the routine performs the processes in steps S30 to S36 including the PM combustion process, as is the case with the first embodiment.

As described above, the system according to the second embodiment detects the average PM diameter and the number of PM particles when the amount of deposited PM is saturated. This ensures that a impedance value to be detected is stable. Thus, the average PM diameter and the number of PM particles can be estimated with increased accuracy.

In the second embodiment, it is assumed that step S40 is performed to judge whether the actual resistance Rm minus the initial resistance Ri is smaller than the first reference resistance ref1. However, the present invention is not limited to the use of a judgment scheme based on resistance values. Any alternative judgment scheme may be employed as far as it judges whether the amount of PM deposited on the electrodes 10 is saturated.

For example, an alternative is to judge whether the amount of deposited PM, which is calculated in step S20, is larger than a reference deposition amount indicative of saturation. Another alternative is to judge whether the amount of change in the actual resistance Rm, which is detected several times at fixed time intervals in step S18, is significantly smaller than a predetermined reference value, and conclude that the amount of deposited PM is saturated when the amount of change in the actual resistance Rm is significantly smaller than the predetermined reference value. Still another alternative is to judge whether the period of time during which the sensor has operated since the end of the last PM combustion process is longer than a reference elapsed time indicative of saturation. In other words, any other judgment scheme may be used as far as it successfully judges whether the amount of deposited PM is saturated.

In the second embodiment, which has been described above, the "saturation judgment means" according to the present invention is implemented when the process in step S40 is performed.

DESCRIPTION OF NOTATIONS

2 PM sensor
8 AC power supply
10 electrodes
12 control device
C1 PM internal capacitance component
C2 PM particle boundary capacitance component
R1 PM internal resistance component
R2 PM particle boundary resistance component
Re electrode resistance component
ref1 first reference resistance
ref2 second reference resistance
Ri initial resistance
Rm actual resistance

The invention claimed is:

1. A particulate matter detection device for measuring particulates in a gaseous body, the device comprising:
    frequency control means for controlling the frequency of an AC voltage applied to a pair of electrodes disposed apart from each other;
    AC impedance detection means for detecting impedances to different frequencies when AC voltages having the different frequencies are applied;
    component calculation means for calculating a resistance component and/or a capacitance component of the impedances to the different frequencies; and
    particulate diameter estimation means for estimating the average diameter and/or the number of particulates in the gaseous body in accordance with changes in the resistance component and/or changes in the capacitance component.

2. The particulate matter detection device according to claim 1,
    wherein, when calculating the resistance component and/or the capacitance component, which each include an intraparticle component and a particle boundary component, the component calculation means calculates the intraparticle component, which is attributable to the internal characteristics of particulates, and the particle boundary component, which is attributable to the interfacial characteristics between particulates, and
    wherein the particulate diameter estimation means estimates the average diameter and/or the number of particulates in accordance with the result of comparison between the intraparticle component and the particle boundary component.

3. The particulate matter detection device according to claim 2, further comprising:
    particulate matter amount estimation means for estimating the amount of particulate matter in the gaseous body in accordance with the intraparticle component and the particle boundary component, which are included in the resistance component.

4. The particulate matter detection device according to claim 2, further comprising:
    inter-electrode resistance detection means for detecting the resistance between the electrodes; and
    particulate matter amount estimation means for estimating the amount of particulate matter in the gaseous body in accordance with the detected inter-electrode resistance.

5. The particulate matter detection device according to claim 4, further comprising:
    saturation judgment means for judging whether the estimated particulate matter amount has reached a reference amount indicative of saturation,
    wherein, when it is concluded that the particulate matter amount has reached the reference amount, the AC impedance detection means performs an impedance detection process.

6. The particulate matter detection device according to claim 1, further comprising:
   inter-electrode resistance detection means for detecting the resistance between the electrodes; and
   particulate matter amount estimation means for estimating the amount of particulate matter in the gaseous body in accordance with the detected inter-electrode resistance.

7. The particulate matter detection device according to claim 6, further comprising:
   saturation judgment means for judging whether the estimated particulate matter amount has reached a reference amount indicative of saturation,
   wherein, when it is concluded that the particulate matter amount has reached the reference amount, the AC impedance detection means performs an impedance detection process.

8. The particulate matter detection device according to claim 1, further comprising;
   particle resistance component calculation means for calculating a particle resistance component, included in the resistance component calculated by the component calculation means, attributable to the internal characteristics and interfacial characteristics of particulates, is distinguished from components attributable to the others; wherein,
   the particulate matter estimation means estimates the amount of particulate matter in accordance with the particle resistance component.

9. A particulate matter detection device for measuring particulates in a gaseous body, the device comprising:
   a frequency controller that controls the frequency of an AC voltage applied to a pair of electrodes disposed apart from each other;
   an AC impedance detector that detects impedances to different frequencies when AC voltages having the different frequencies are applied;
   a component calculator that calculates a resistance component and/or a capacitance component of the impedances to the different frequencies; and
   a particulate diameter estimator that estimates the average diameter and/or the number of particulates in the gaseous body in accordance with changes in the resistance component and/or changes in the capacitance component.

* * * * *